United States Patent
Riley et al.

(10) Patent No.: US 6,704,956 B2
(45) Date of Patent: Mar. 16, 2004

(54) HOSPITAL BED EQUIPMENT SUPPORT APPARATUS

(75) Inventors: Carl W. Riley, Milan, IN (US); Troy D. Action, Saint Paul, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 10/224,201

(22) Filed: Aug. 20, 2002

(65) Prior Publication Data

US 2003/0037375 A1 Feb. 27, 2003

Related U.S. Application Data

(60) Provisional application No. 60/314,483, filed on Aug. 23, 2001, and provisional application No. 60/333,387, filed on Nov. 26, 2001.

(51) Int. Cl.⁷ .............................................. A61G 7/05
(52) U.S. Cl. ............................. 5/600; 5/658; 5/503.1
(58) Field of Search ..................... 5/658, 503.1, 600, 5/607, 620

(56) References Cited

U.S. PATENT DOCUMENTS

| | | | |
|---|---|---|---|
| 383,815 A | 5/1888 | Kilborn |
| 1,290,809 A | 1/1919 | Truax |
| 1,490,650 A | 4/1924 | Wagner |
| 1,674,081 A | 6/1928 | Adams |
| 1,919,114 A | 7/1933 | Ley |
| 2,470,524 A | 5/1949 | Scudder |
| 2,673,771 A | 3/1954 | Krewson |
| 2,696,963 A | 12/1954 | Shepherd |
| RE24,290 E | 3/1957 | MacKnight |
| 3,004,743 A | 10/1961 | Wenger |
| 3,402,947 A | 9/1968 | Lewis |
| 3,552,577 A | 1/1971 | Latham, Jr. |
| 3,588,023 A | 6/1971 | Cohen |
| 3,674,294 A | 7/1972 | Kirkham |
| 3,814,023 A | 6/1974 | Stantial |
| 4,005,844 A | 2/1977 | Richmond |
| 4,113,222 A | 9/1978 | Frinzel |
| 4,163,536 A | 8/1979 | Heller et al. |
| 4,190,224 A | 2/1980 | LeBlanc et al. |
| 4,225,104 A | 9/1980 | Larson |
| 4,262,872 A | 4/1981 | Kodet |

(List continued on next page.)

FOREIGN PATENT DOCUMENTS

| | | |
|---|---|---|
| DE | 299 03 222 U1 | 6/1999 |
| EP | 0 893 557 A1 | 7/1998 |
| WO | WO 93/12346 | 6/1993 |
| WO | WO 98/02107 | 1/1998 |
| WO | WO 01/86575 | 11/2001 |

*Primary Examiner*—Frederick L. Lagman
(74) *Attorney, Agent, or Firm*—Bose McKinney & Evans LLP

(57) ABSTRACT

An equipment support for use with a patient assist apparatus having a signal source includes a receptacle adapted to mount to the patient assist apparatus having a plurality of contacts adapted to receive signals from the signal source and a cavity, and a support body or pole having an equipment mount on one end and a plug on the other end for being removably inserted into the cavity. The plug includes a plurality of contacts that are connected to conductors that extend through the support body to the equipment mount to provide the signals from the signal source to equipment mounted on the equipment mount. The plug contacts and receptacle contacts are arranged such that all of the plug contacts contact their corresponding receptacle contacts as the plug is inserted into the receptacle.

49 Claims, 15 Drawing Sheets

U.S. PATENT DOCUMENTS

| | | | |
|---|---|---|---|
| D260,816 S | 9/1981 | Zissimopoulos et al. | |
| 4,339,104 A | 7/1982 | Weidman | |
| 4,511,157 A | 4/1985 | Wilt, Jr. | |
| 4,511,158 A | 4/1985 | Varga et al. | |
| 4,559,036 A | 12/1985 | Wunsch | |
| 4,600,209 A | 7/1986 | Kerr, Jr. | |
| 4,616,797 A | 10/1986 | Cramer | |
| 4,629,074 A | 12/1986 | Toder | |
| D289,604 S | 5/1987 | Gallant et al. | |
| 4,691,397 A | 9/1987 | Netzer | |
| 4,702,448 A | 10/1987 | LoJacono et al. | |
| 4,718,892 A | 1/1988 | Yung-Ho | |
| 4,729,576 A | 3/1988 | Roach | |
| 4,744,536 A | 5/1988 | Bancalari | |
| 4,768,241 A * | 9/1988 | Beney | 5/658 |
| 4,905,882 A | 3/1990 | Ross | |
| 4,905,944 A | 3/1990 | Jost et al. | |
| 4,925,444 A | 5/1990 | Orkin et al. | |
| 4,945,592 A | 8/1990 | Sims et al. | |
| 4,966,340 A | 10/1990 | Hunter | |
| 4,969,768 A | 11/1990 | Young | |
| 4,997,150 A | 3/1991 | Mardollo | |
| 5,016,307 A | 5/1991 | Rebar | |
| 5,023,967 A * | 6/1991 | Ferrand | 5/607 |
| 5,078,349 A | 1/1992 | Smith | |
| 5,083,807 A | 1/1992 | Bobb et al. | |
| 5,094,418 A | 3/1992 | McBarnes, Jr. et al. | |
| 5,108,066 A | 4/1992 | Lundstrom | |
| 5,110,076 A | 5/1992 | Snyder et al. | |
| 5,112,019 A | 5/1992 | Metzler et al. | |
| 5,125,607 A | 6/1992 | Pryor | |
| 5,174,533 A | 12/1992 | Pryor et al. | |
| 5,207,642 A | 5/1993 | Orkin et al. | |
| 5,224,681 A | 7/1993 | Lundstrom | |
| 5,319,816 A | 6/1994 | Ruehl | |
| 5,322,253 A | 6/1994 | Stevens | |
| 5,335,384 A * | 8/1994 | Foster et al. | 5/658 |
| 5,400,995 A | 3/1995 | Boyd | |
| 5,407,163 A | 4/1995 | Kramer et al. | |
| 5,542,138 A | 8/1996 | Williams et al. | |
| 5,588,166 A | 12/1996 | Burnett | |
| 5,592,153 A | 1/1997 | Welling et al. | |
| 5,636,823 A | 6/1997 | Boyd | |
| 5,647,491 A | 7/1997 | Foster et al. | |
| 5,657,884 A | 8/1997 | Zilincar, III | |
| 5,699,988 A | 12/1997 | Boettger et al. | |
| 5,704,577 A | 1/1998 | Gordon | |
| 5,772,162 A | 6/1998 | Lin | |
| 5,820,086 A | 10/1998 | Hoftman et al. | |
| 5,826,847 A | 10/1998 | Warner et al. | |
| 5,857,685 A | 1/1999 | Phillips et al. | |
| 5,888,014 A | 3/1999 | Lung et al. | |
| 6,224,027 B1 | 5/2001 | Johnson et al. | |

* cited by examiner

HOSPITAL BED EQUIPMENT SUPPORT APPARATUS

RELATED APPLICATIONS

This application claims the benefit of U.S. Provisional Patent Application Ser. No. 60/314,483, filed Aug. 23, 2001, and U.S. Provisional Patent Application Ser. No. 60/333,387, filed Nov. 26, 2001, the disclosures of which are hereby expressly incorporated herein by reference.

FIELD OF THE INVENTION

The present invention generally relates to devices for supporting equipment used with patient assist apparatuses, and more particularly to a device for supporting patient care equipment and providing electrical connections thereto from a receptacle attached to the patient assist apparatus which removably receives the support.

BACKGROUND OF THE INVENTION

Patient assist apparatuses, such as hospital beds, are typically provided with or connected to medical equipment, such as control pendants, monitors/interface devices, etc. Conventional pendants are generally electrically connected to the control circuitry of the bed by a cable which permits placement of the pendant at various locations on the bed. Interface devices are generally mounted to the side rails or the head or foot board of the bed, and electrically hardwired to the bed electronics.

It is desireable to have maximum flexibility in terms of locating and relocating such medical equipment to accommodate access to the patient by medical personnel, placement of other monitoring and treatment equipment, and re-positioning of the patient. While conventional pendants are easily moved between various locations, the cable may become tangled, or otherwise impede access to the patient, placement of other equipment, and movement of the patient.

Additionally, interface devices may be difficult to use or inconviently located when provided at a fixed location on the bed. For example, if an interface device is mounted to a bed side rail which must be folded down, the interface may be rendered essentially useless. If the interface is mounted to the foot board, medical personnel positioned at the head of the bed must relocate to use the interface.

SUMMARY OF THE INVENTION

The present invention provides an equipment support device for use with a patient assist apparatus which may include a plurality of receptacles mounted at various locations on the apparatus for removably receiving a support body to which is mounted equipment, such as a control pendant and/or an interface device. The receptacles may include a cavity and a plurality of contacts extending into the cavity and being connected to the control circuitry of the apparatus. The support body may include a plug at one end having a plurality of contacts configured to mate with the receptacle contacts when the plug is seated in the receptacle cavity. Conductors extend from the plug contacts to the equipment mounted to the support body. Accordingly, medical personnel may locate the equipment support device at any of the receptacle locations around the patient assist apparatus by inserting the support body plug into the desired receptacle, thereby electrically connecting the equipment mounted to the equipment support device to the apparatus control circuitry and mechanically supporting the equipment in a desired location.

In an alternate embodiment, the receptacles may include power and signal windings that loop around the central cavity of the receptacle. These windings form one side of a pair of transformers, one for supplying power to the support body, and one for supplying other signals to the support body. The support body plug includes corresponding secondary windings that complete the pair of transformer circuits, and are connected to conductors that supply power and other signals to the equipment mounted to the support body. In this embodiment, the receptacle contacts and the plug contacts are eliminated. Power and other signals are provided to the equipment with electrical isolation. Additionally, a spring-loaded detent is provided in each of the receptacles for cooperating with a lock ring on the support body plug to mechanically retain the plug in the receptacle when the plug is in a seated position.

The features of the present invention described above, as well as additional features, will be readily apparent to those skilled in the art upon reference to the following description and the accompanying drawings.

DETAILED DESCRIPTION OF EMBODIMENTS OF THE INVENTION

The exemplary embodiments selected for description below are not intended to limit the invention to the precise forms disclosed. Instead, the embodiments have been selected for description to enable one of ordinary skill in the art to practice the invention.

Figure 1:
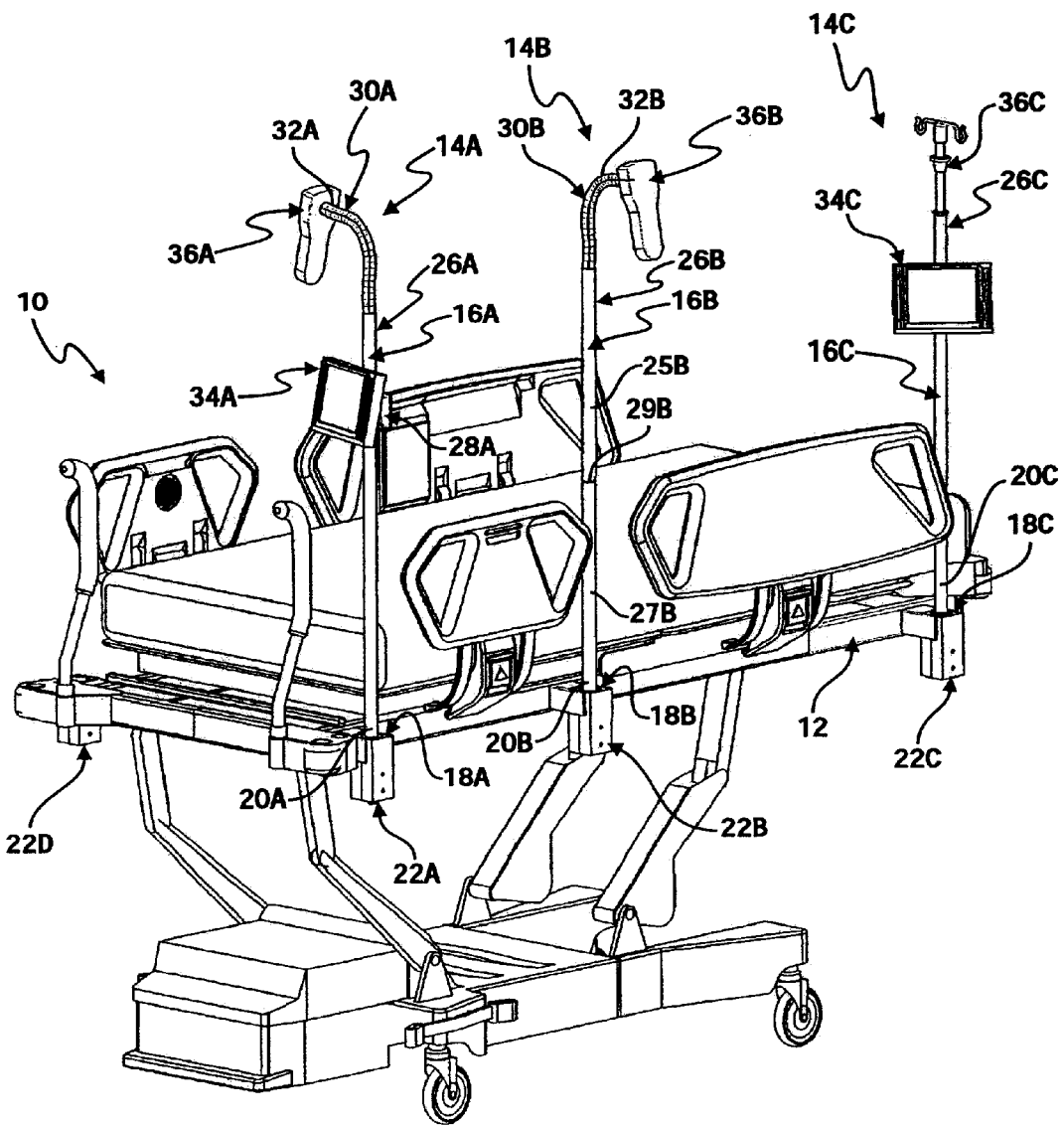
FIG. 1 is a perspective view of a patient assist apparatus having a plurality of equipment support apparatuses attached thereto.

FIG. 1 shows a hospital bed 10 that has a variety of conventional components including a frame 12. Three embodiments of an equipment support apparatus according to the present invention 14A–C are shown attached to frame 12. Equipment supports 14A, 14B, and 14C differ in various ways which will be described in detail below. In general, however, each equipment support 14A, 14B, and 14C includes a support body 16A–C, a plug 18A–C at one end 20A–C of support body 16A–C, and a receptacle 22A–C attached to frame 12.

Support body 16A of equipment support 14A may be formed from a generally rigid hollow pole, and includes an equipment end 26A opposite end 20A. Equipment support 14A also includes an equipment mount 28A connected to equipment end 26A of support body 16A. A goose neck or flexible portion 30A having a free end 32A is also connected to equipment end 26A of support body 16A. An interface 34A is physically and electrically connected to equipment mount 28A as is further described below. Interface 34A (and interface 34C) may be a display, a control panel, or any other type of interface or monitor. Similarly, a pendant 36A is physically and electrically connected to free end 32A of flexible portion 30A as is further described below. The position of pendant 36A may be adjusted by moving the pendant within the range of positions provided by the flexibility of flexible portion 30A. It should be understood that equipment mount 28A may be movably or adjustably mounted on support body 16A such that interface 34A may be moved upwardly and downwardly on support body 16A, rotated about support body 16A, and tilted relative to support body 16A. If such adjustability is provided, then the electrical conductors or wires connecting equipment mount 28A (and interface 34A) to plug 18A, further described below, may extend through an opening or slot in support body 16A and have sufficient slack and/or flexibility to accommodate the full range of adjustment of equipment mount 28A.

Equipment support 14B similarly includes a support body 16B with an equipment end 26B, a flexible portion 30B having a free end 32B, and a pendant 36B mechanically and electrically connected to free end 32B of flexible portion 30B. Unlike support body 16A, support body 16B does not include an equipment mount or interface. Also, support body 16B includes a first section 25B and a second section 27B. First section 25B is connected to second section 27B at a telescopic joint 29B. Telescopic joint 29B permits adjustment of the height of pendant 36B above bed 10. In other words, as one of first section 25B or second 27B is telescopically received within the other section, the overall height of support body 16B is reduced. As will be further described below, conductors (not shown) extend between pendant 36B and plug 18B (through flexible portion 30B and support body 16B) to permit communication between electronics on pendant 36B and other portions of bed 10. Obviously, the conductors (not shown) connecting pendant 36B to plug 18B must have sufficient slack and/or flexibility to accommodate the full range of adjustment of support body 16B. Additionally, the position of pendant 36B may be adjusted within the range of positions provided by flexible portion 30B.

Equipment support 14C also includes a support body 16C with an equipment mount (not shown) for mounting an interface 34C at equipment end 26C of support body 16C. A standard, telescopically extendable IV bag hook 36C is received by equipment end 26C of support body 16C. Like support bodies 16A and 16B, support body 16C includes conductors (not shown) which extend between the equipment mount (not shown) and plug 18C.

Also shown in FIG. 1 is a fourth receptacle 22D mounted to the perimeter of frame 12. Additional receptacles may be mounted at other locations on frame 12 to permit relocation of any of equipment supports 14A–C. As is further described below, electrical contacts in receptacles 22A–D provide power and other signals to interfaces 34A, 34C, and pendants 36A, 36B. When receptacles 22A–D are mounted to frame 12, these electrical contacts may be hard-wired to the control circuitry of bed 10.

Figure 2B:
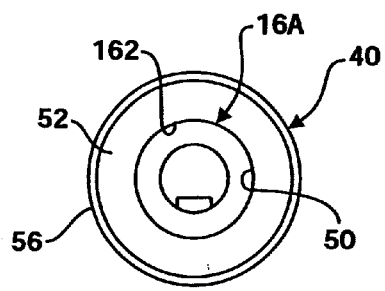
FIG. 2B is a top plan view of the equipment support apparatus shown in FIG. 2A.
Figure 2A:
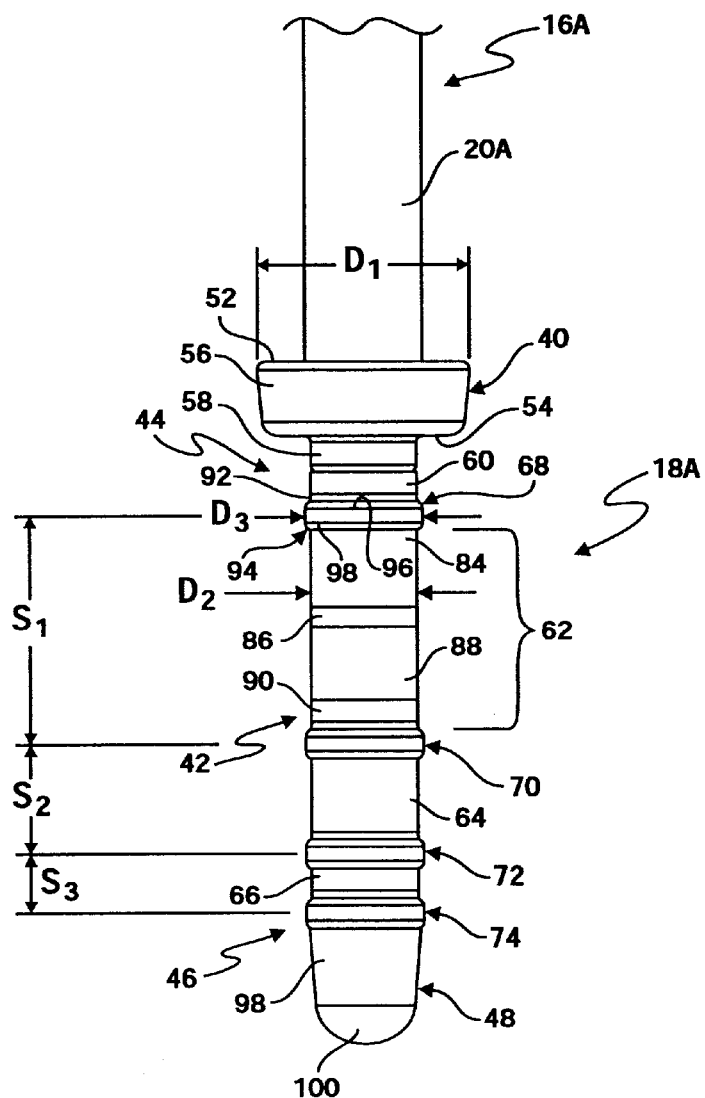
FIG. 2A is a partially fragmented, side elevational view of a portion of an equipment support apparatus according to the present invention.

FIGS. 2A and 2B show a plug according to the present invention. Since plugs 18A–C of equipment supports 14A–C are identical, only one plug is described below. Plug 18A generally includes a stop 40 which is connected to end 20A of support body 16A, and a substantially cylindrical, elongated body 42 including an end 44 connected to stop 40 and an end 46 connected to a tip 48. Tip 48 is formed of a non-conductive material and includes a slightly tapered outer surface 98 which terminates in a rounded dome 100. As shown in FIG. 2A, support body 16A, stop 40, plug body 42, and tip 48 are substantially coaxial.

Stop 40 is an annular, ring-shaped member having a central opening 50 (FIG. 2B) that receives support body 16A, an upper surface 52, a lower surface 54, and an outer surface 56 which tapers slightly from upper surface 52 to lower surface 54. A cylindrical extension 58 protrudes from lower surface 54 of stop 40 and is connected to end 44 of plug body 42.

Figure 3:
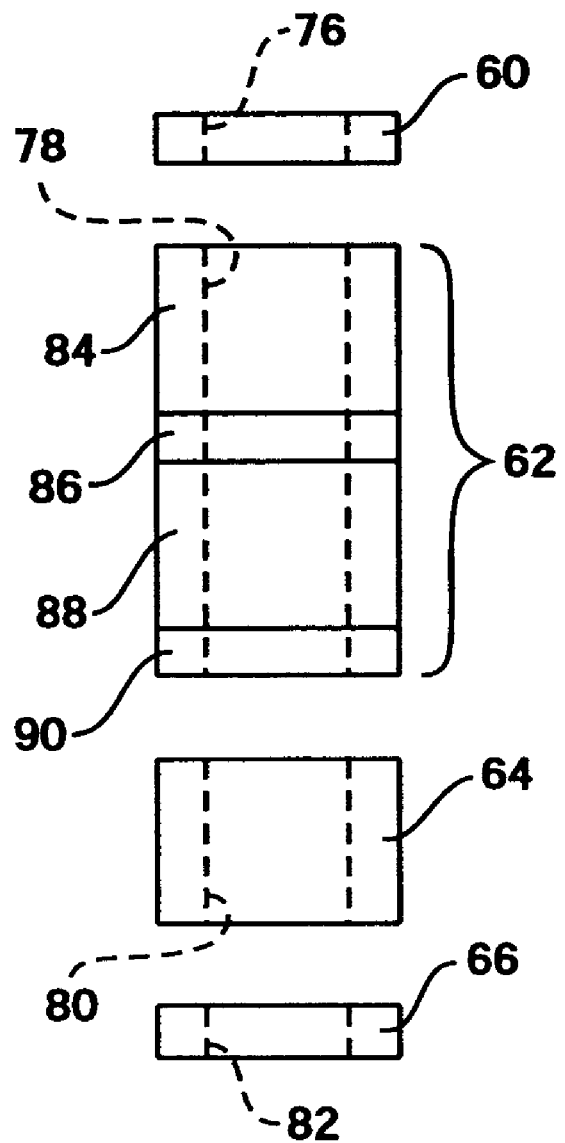
FIG. 3 is a side elevational view of components of an equipment support apparatus according to the present invention.

Plug body 42 includes insulators 60, 62, 64, 66, and contacts 68, 70, 72, 74. As best shown in FIG. 3, insulators 60, 62, 64, 66 are substantially cylindrical with central openings 76, 78, 80, 82, respectively. As should be apparent from the figures, spacers 60, 62, 64, 66 include annular members having one of two lengths. Specifically, spacers 60 and 66 are identical in length and shorter than spacer 64. Spacer 62 is an assembly of four spacer sections 84, 86, 88, 90. Spacer sections 86 and 90 are identical to spacers 60 and 66. Spacer sections 84 and 88 are identical to spacer 64. Accordingly, spacers having any of a variety of different lengths may be assembled using two standard length spacer sections. It should be understood that stop 40, tip 48, and all of the components of plug body 42 may be assembled in any of a variety of ways. For example, each piece could include appropriately threaded male and female portions (not shown), or simply be formed as slip rings to be received over a common inner sleeve (not shown).

Referring again to FIG. 2A, spacers 60, 62, 64, 66 have substantially the same outer diameter $D_2$, which is smaller than the outer diameter $D_1$ of stop 40. First contact 68 is located between spacer 60 and spacer 62. Second contact 70 is located between spacer 62 and spacer 64. Third contact 72 is located between spacer 64 and spacer 66. Finally, fourth contact 74 is located between spacer 66 and tip 48.

Contacts 68, 70, 72, and 74 are substantially identical. Therefore, only one is labeled in FIG. 2A. Each of contacts 68, 70, 72, and 74 include an annular portion 92 and a retention ring 94 having a diameter $D_3$ which is larger than diameter $D_2$ and smaller than diameter $D_1$. Retention rings 94 have a chamfered upper edge 96 and a chamfered lower edge 98. Retention rings 94 may be either conductive or non-conductive. Likewise, portions 92 may be either conductive or non-conductive. In the embodiment described, portions 92 are non-conductive and retention rings 94 are conductive. As shown in FIG. 2A, the spacings $S_1$, $S_2$, $S_3$ between retention rings 94 of contacts 68, 70, 72, and 74 are all different as a result of the different lengths of spacers 62, 64, and 66. This prevents shorting and erroneous connections during insertion and removal of plug 18A into and out of receptacle 22A as will be further described below.

Each retention ring 94 of contacts 68, 70, 72, and 74 is connected to a respective conductor (FIGS. 6A and 6B) which extends within the central opening formed through the spacers and conductors, central opening 50 of stop 40, and a central opening 162 of support body 16A.

Figure 4B:
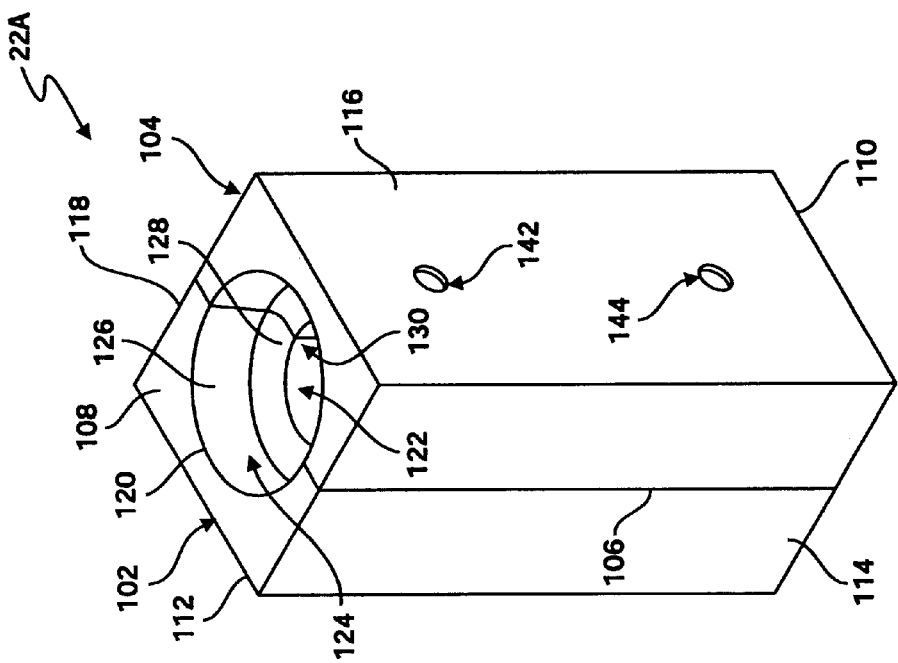
FIGS. 4A and 4B are perspective views of a receptacle of an equipment support apparatus according to the present invention.
Figure 4A:
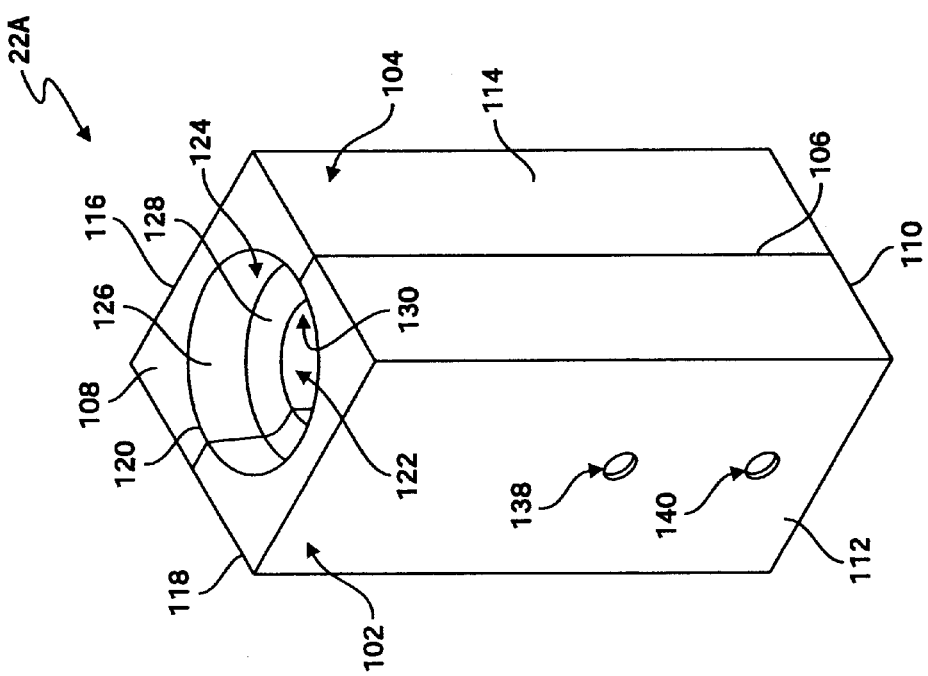
Figure 4D:
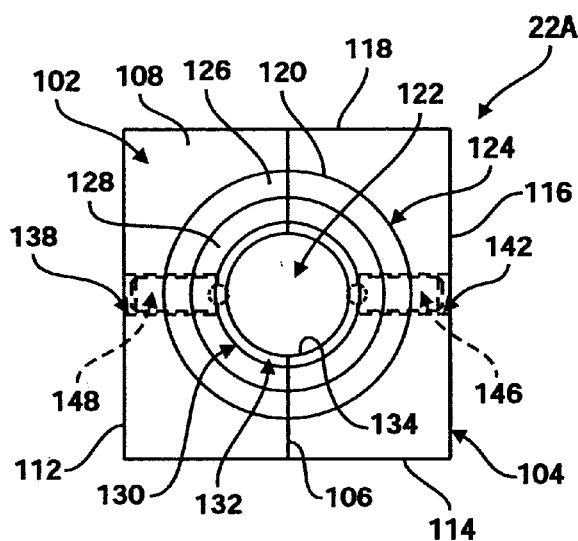
FIG. 4D is a top plan view of the receptacle shown in FIGS. 4A–C.
Figure 4C:
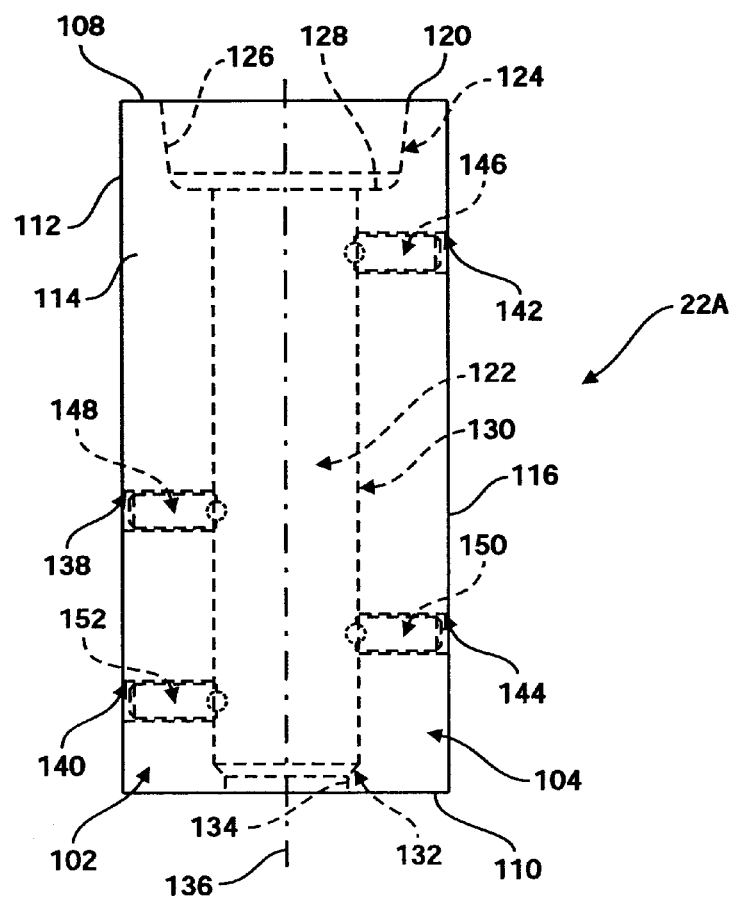
FIG. 4C is a side elevational view of the receptacle shown in FIGS. 4A and 4B.

An illustrative receptacle 22A is shown in FIGS. 4A–4D. Receptacle 22A generally includes a first half 102 and a second half 104 that may be assembled separately and attached together at interface 106 using any of a variety of conventional attachment techniques. Once joined, halves 102, 104 form a six-sided body having an upper surface 108, a lower surface 110 and side surfaces 112, 114, 116, 118. A central opening 120 is formed in upper surface 108. A cavity generally referred to by numeral 122 extends from opening 120 through receptacle 22A to bottom surface 110. As best shown in FIG. 4C, cavity 122 includes an enlarged diameter portion 124 having a cylindrical, slightly tapered side surface 126 and a shoulder surface 128 which is substantially parallel to upper surface 108 of receptacle 22A. Cavity 122 further includes an elongated central portion 130, a tapered lower portion 132, and a lower opening 134 formed in lower surface 110 of receptacle 22A. Cavity 122 is generally cylindrical and includes a central axis 136.

As best shown in FIGS. 4A–4D, half 102 of receptacle 22A includes a pair of bores 138, 140 which are substantially vertically aligned on side surface 112 and extend into cavity 122. Similarly, half 104 of receptacle 22A includes bores 142, 144 which are substantially vertically aligned and extend from side surface 116 into cavity 122. As best shown in FIG. 4D, bores 138, 140, 142, 144 lie in substantially the same plane when halves 102, 104 are assembled. As best shown in FIG. 4C, a first detent contact 146 is installed in bore 142, a second detent contact 148 is installed in bore 138, a third detent contact 150 is installed in bore 144, and a fourth detent contact 152 is installed in bore 140. Detent contacts 146, 148, 150, 152 may be conventional, off-the-shelf ball and spring detent assemblies. Each detent contact is connected via a wire (not shown) to the control circuitry of bed 10.

Figure 5:
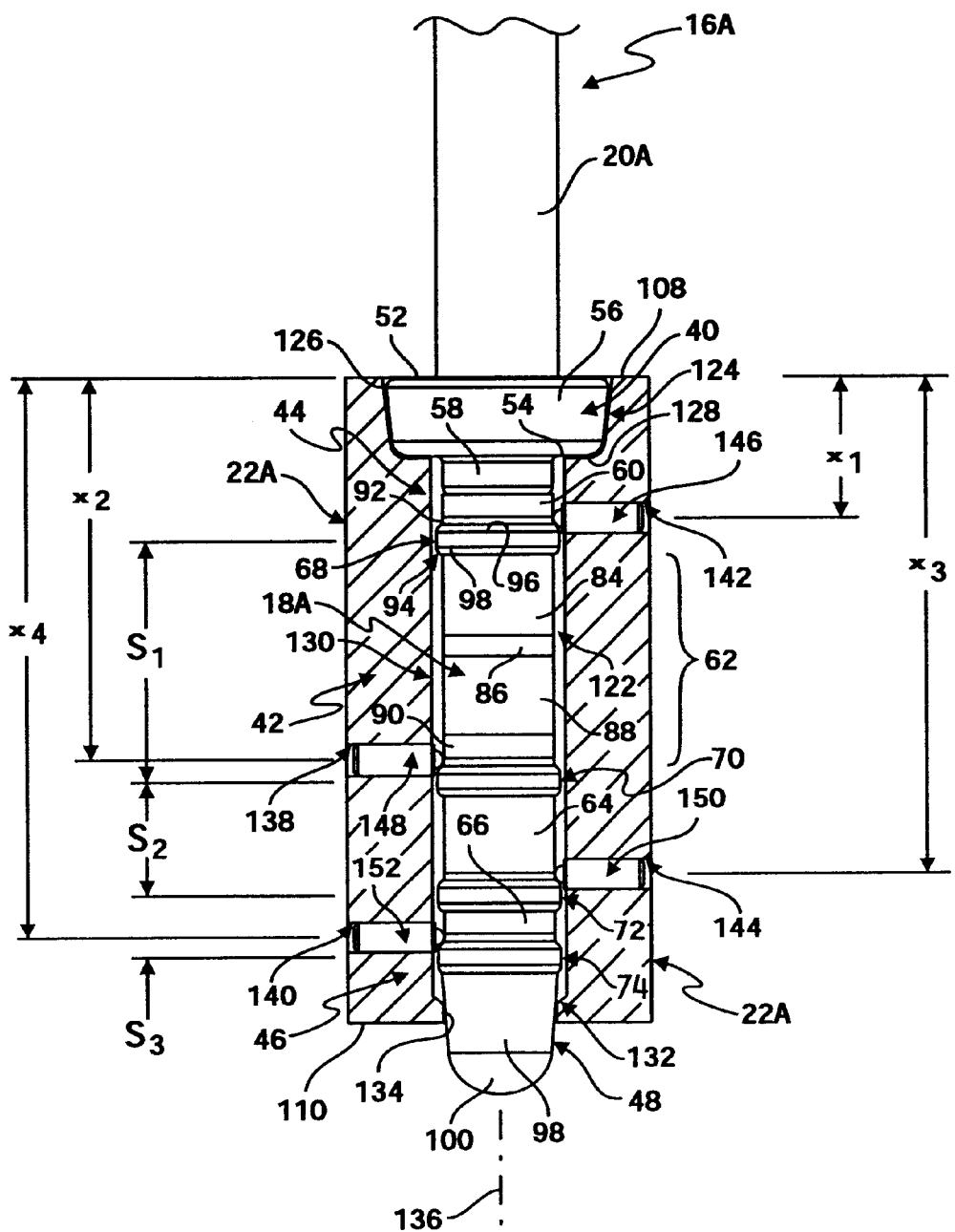
FIG. 5 is a partially fragmented, side elevational view, partly in section, of a portion of an equipment support apparatus according to the present invention.

Referring now to FIG. 5, plug 18A is shown in a seated position wherein substantially the entire plug body 42 is inserted into cavity 122. When plug 18A is so positioned within cavity 122, detent contacts 146, 148, 150, and 152 of receptacle 22A make electrical contact with retention rings 94 of plug body contacts 68, 70, 72, 74, respectively. Bore 142 and detent contact 146 are spaced a distance $X_1$ from upper surface 108 of receptacle 22A. Similarly, bore 138 and detent contact 148 are spaced a distance $X_2$ from upper surface 108, bore 144 and detent contact 150 are spaced a distance $X_3$ from upper surface 108, and bore 140 and detent contact 152 are spaced a distance $X_4$ from upper surface 108. The difference between distances $X_2$ and $X_1$ corresponds to spacing $S_1$. Likewise, the difference between distances $X_3$ and $X_2$ corresponds to spacing $S_2$. Finally, the difference between distances $X_4$ and $X_3$ corresponds to spacing $S_3$. Since detent contacts 146, 148, 150, 152 are spaced to correspond with the spacings $S_1$, $S_2$, $S_3$ between plug contacts 68, 70, 72, 74, when plug 18A is in the seated position shown in FIG. 5, electrical connections are made between detent contact 146 and contact 68, detent contact 148 and contact 70, detent contact 150 and contact 72, and detent contact 152 and contact 74. Because spacings $S_1$, $S_2$, $S_3$ are different from one another, as plug 18A is inserted downwardly into cavity 122 of receptacle 22A, all of detent contacts 146, 148, 150, 152 simultaneously contact their respective plug contacts 68, 70, 72, 74 when plug 18A substantially reaches the seated position, but not during insertion or removal of plug 18A.

As should be apparent from FIG. 5, as plug 18A is moved downwardly, the balls of detent contacts 146, 148, 150, 152 are urged outwardly from central axis 136 by rings 94 of plug contacts 68, 70, 72, 74. Electrical contact is established as soon as rings 94 contact the balls of detent contacts 146, 148, 150, 152. As a ring 94 moves past a detent contact 146, 148, 150, 152, the ball of the detent contact cams over chamfered edge 98 and down chamfered edge 96 of ring 94. When plug 18A is in the seated position, each of the balls is spring biased outwardly against portions 92. Rings 94 remain in electrical contact with the balls and provide a locking function to resist removal of plug 18A upwardly out of cavity 122. Specifically, sufficient upward force must be applied to support body 16A to overcome the force exerted against plug 18A by the balls, which force resists upward movement as the balls cam over chamfered edge 96 of retention rings 94. As shown in FIG. 5, detent contacts 146, 150 are opposed to detent contacts 148, 152 so that the spring force urging the balls of one pair of the detent contacts is in substantial opposition to the spring force urging the balls of the other pair of detent contacts toward plug body 42, thereby providing a better "grip" on plug 18A. Additionally, it should be noted that by providing spring biased detent contacts 146, 148, 150, 152, the present invention may provide more reliable electrical connections than would a receptacle and plug assembly using friction fit connections.

As should also be apparent from FIG. 5, as plug 18A is inserted downwardly in cavity 122, tip 48 guides plug 18A and maintains substantial vertical alignment along central axis 136 of cavity 122. As plug 18A approaches the seated position shown in FIG. 5, dome surface 100 and tapered surface 98 of tip 48 guide plug 18A along tapered lower portion 132 and through opening 134. Further downward movement of plug 18A is prevented by stop 40. Specifically, lower surface 54 of stop 40 engages shoulder surface 128 of enlarged diameter portion 124 of cavity 122, thereby preventing further downward movement. Tapered surface 56 of stop 40 cooperates with tapered side surface 126 of cavity 122 to center and guide plug 18A into cavity 122 as plug 18A approaches the seated position.

Figure 6B:
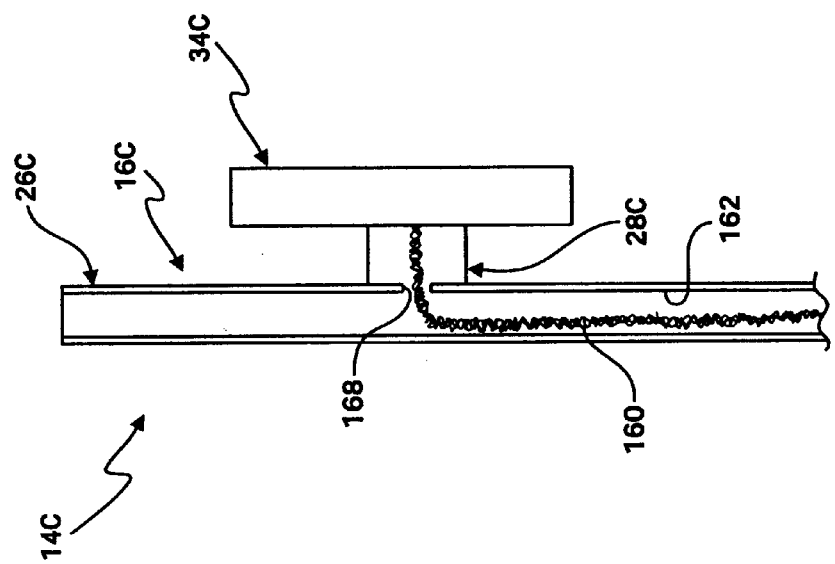
FIGS. 6A and 6B are partially fragmented, side elevational views, partly in section, depicting the electrical connections of embodiments of an equipment support apparatus according to the present invention.
Figure 6A:
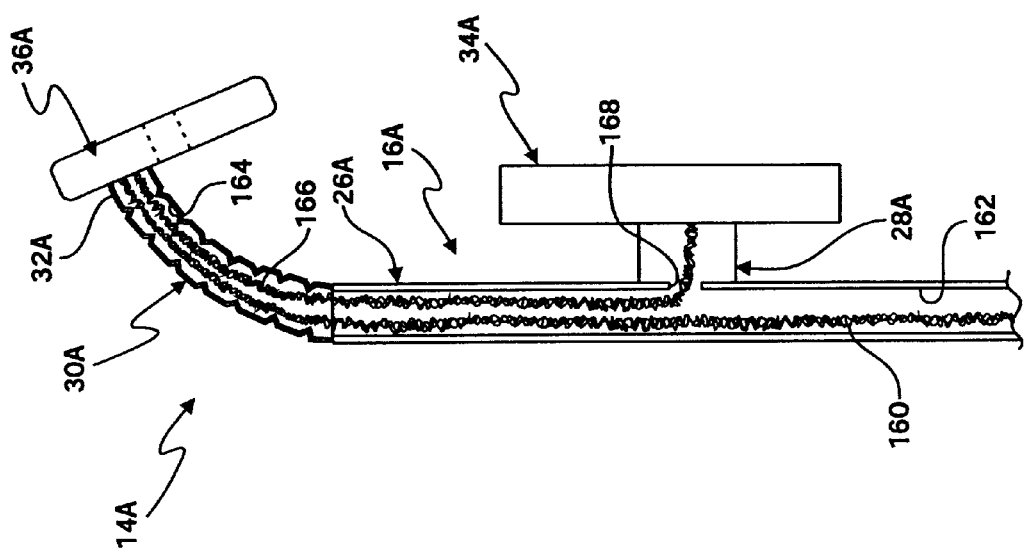

Referring now to FIGS. 6A and 6B, wires or conductors 160 are connected to plug contacts 68, 70, 72, and 74, respectively. Specifically, each conductor 160 is connected to a separate ring 94 of contacts 68, 70, 72, 74. FIG. 6A illustrates the routing of conductors 160 for equipment support 14A, also shown in FIG. 1. Conductors 160 extend through central opening 162 in support body 16A, through equipment end 26A and a hollow interior 164 of flexible portion 30A to pendant 36A. Conductors 160 may provide power and other signals to pendant 36A from receptacle 18A, and pendant 36A may provide signals through conductors 160 to receptacle 18A. For example, a patient may press a call button on pendant 36A which sends a signal through conductors 160 to receptacle 18A and equipment associated with bed 10 according to principles well known in the art. Conductors 166 extend from pendant 36A through hollow interior 164 of flexible portion 30A, central opening 162 of support body 16A, and an opening 168 formed in support body 16A to equipment mount 28A. Conductors 166 are connected to interface 34A at equipment mount 28A using appropriate connectors. Accordingly, power and other signals may be routed between receptacle 18A and interface 34A through equipment mount 28A and pendant 36A.

FIG. 6B reflects the basic conductor routing of equipment support 14C (FIG. 1) which does not include a pendant. IV bag hook 36C of equipment support 14C, shown in FIG. 1, is not shown in FIG. 6B. FIG. 6B shows conductors 160 from plug contacts 68, 70, 72, 74 routed directly to interface 34C through central opening 162 of support body 16C, opening 168, and equipment mount 28C. It should be understood from the foregoing that the conductor routing of equipment support 14B (which includes only a pendant and no interface) is the same as that shown in FIG. 6A except that conductors 166 are unnecessary.

FIGS. 7–10 depict an alternate embodiment of an equipment support apparatus according to the present invention. Various components of the alternate embodiment described below are similar to the components described with reference to the previous figures. Accordingly, the reference designations of like components have been retained, but increased by 200. FIGS. 7A and 7B show an alternate embodiment of a plug 218 according to the present invention. Plug 218 generally includes a stop 240 that is connected to an end 220 of support body 216, and a substantially cylindrical, elongated body 242 including an end 244 connected to stop 240 and an end 246 connected to a tip 248. Body 242, stop 240, and tip 248 are formed of a non-conductive material. Tip 248 includes a slightly tapered outer surface 298 which terminates in a rounded dome 300. As shown, support body 216, stop 240, plug body 242, and tip 248 are substantially coaxial.

Figure 7B:
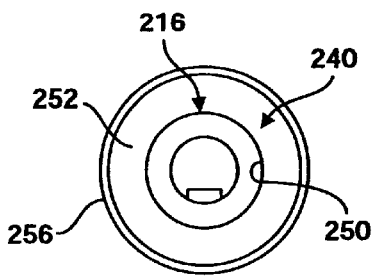
FIG. 7B is a top plan view of the equipment support apparatus shown in FIG. 7A.
Figure 7A:
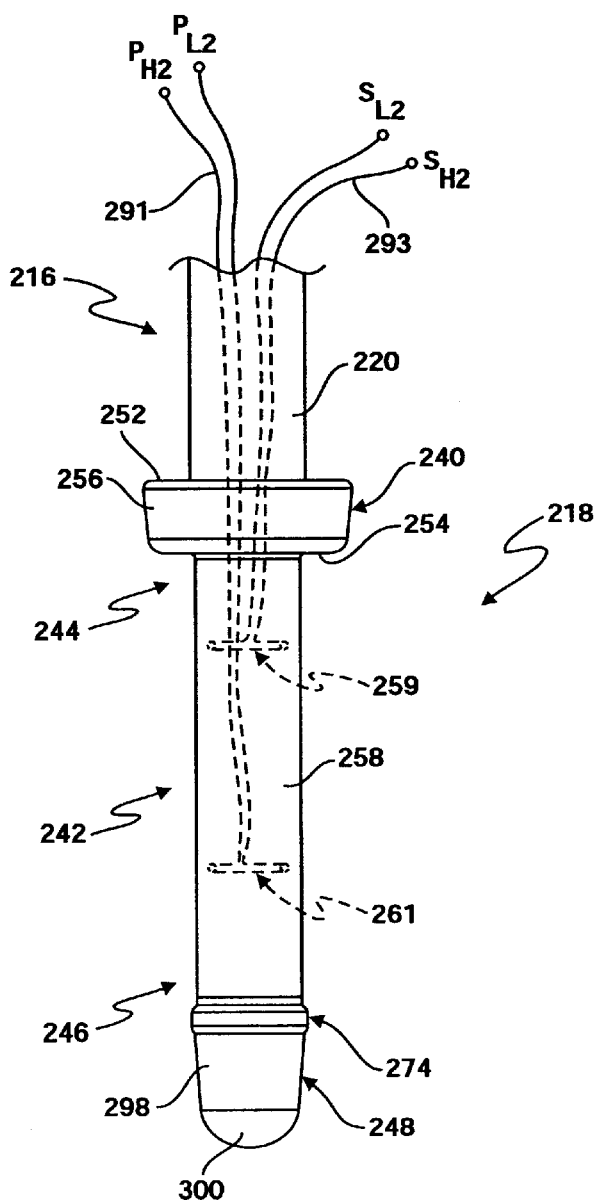
FIG. 7A is a partially fragmented, side elevational view of a portion of another embodiment of an equipment support apparatus according to the present invention.

Stop 240 is an annular, ring-shaped member having a central opening 250 (FIG. 7B), an upper surface 252, a lower surface 254, and an outer surface 256 which tapers slightly from upper surface 252 to lower surface 254. A cylindrical extension 258 extends from lower surface 254 to tip 248, and carries an increased diameter retention ring 274. In FIG. 7A, retention ring 274 is shown positioned adjacent tip 248. It should be understood, however, that retention ring 274 may be located anywhere along the length of extension 258.

A first conductor 291 extends from end $P_{H2}$, through support body 216 and central opening 250 of plug 218 to a location within extension 258 of plug body 242. Conductor 291 forms a loop 261 embedded within the non-conductive material of extension 258 adjacent the outer surface of extension 258. The other end of conductor 291 extends back through central opening 250 and support body 216 to end $P_{L2}$. Similarly, a second conductor 293 extends from end $S_{H2}$, through support body 216 and central opening 250 to form a loop 259 within extension 258 adjacent the outer surface of extension 258. Conductor 293 also extends back through opening 250 to end $S_{L2}$. As will be further described below, loops 259, 261 each form one side of a transformer circuit.

Figure 8B:
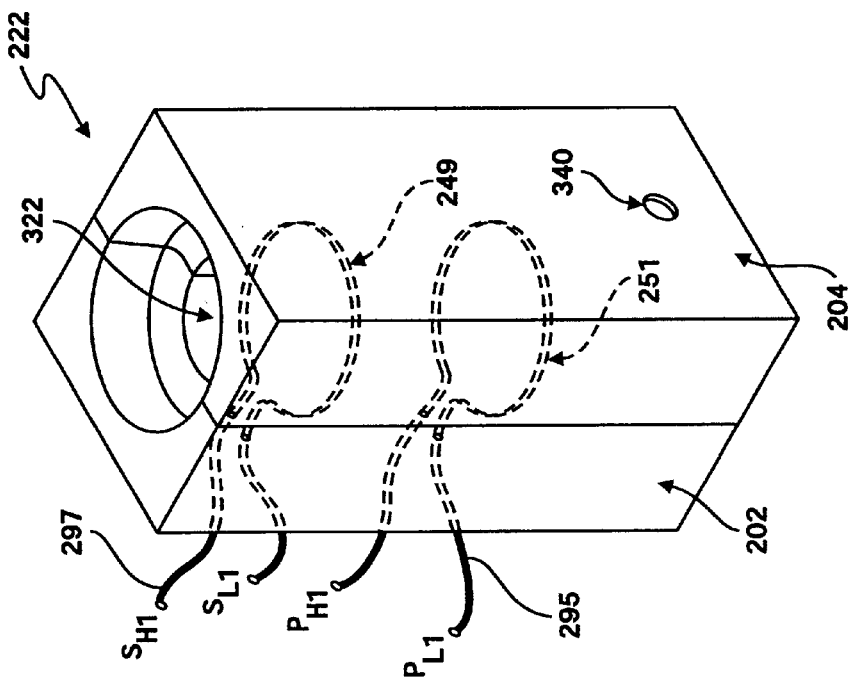
FIGS. 8A and 8B are perspective views of another embodiment of a receptacle of an equipment support apparatus according to the present invention.
Figure 8A:
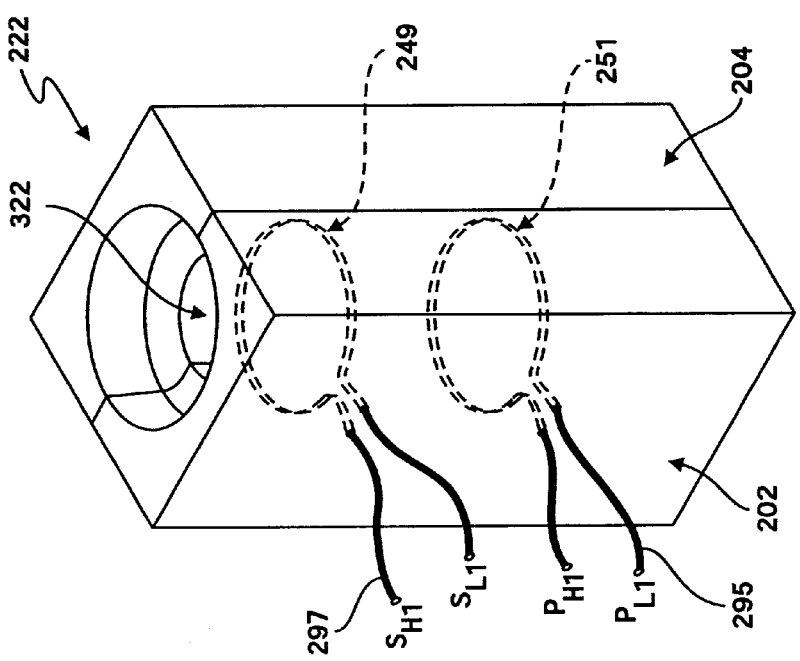
Figure 8D:
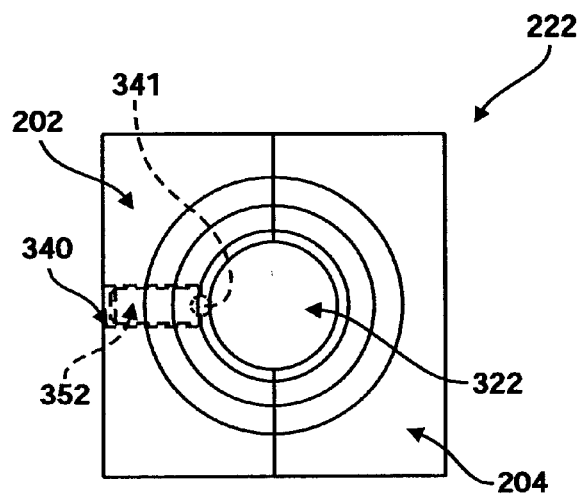
FIG. 8D is a top plan view of the receptacle shown in FIGS. 8A–C.
Figure 8C:
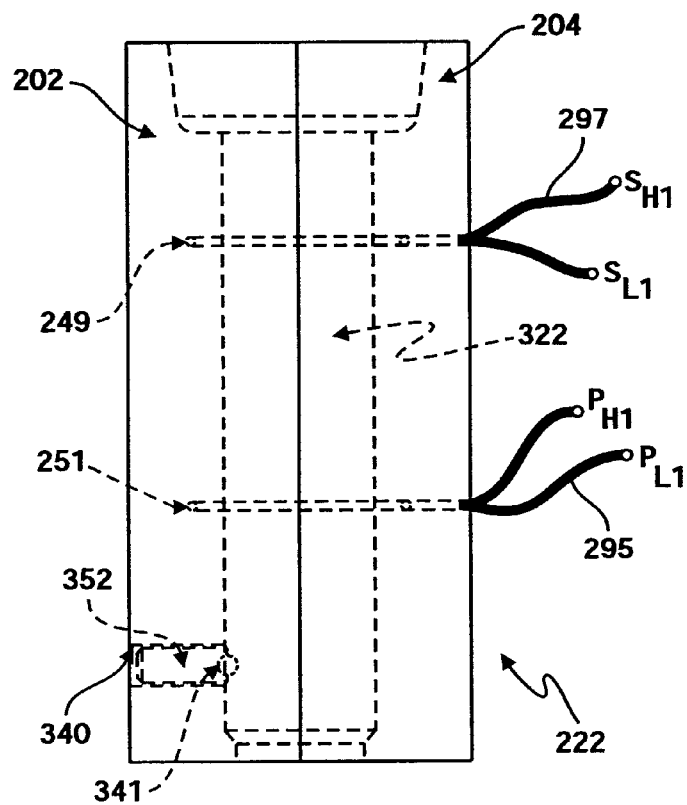
FIG. 8C is a side elevational view of the receptacle shown in FIGS. 8A and 8B.

FIGS. 8A–8D show an alternate embodiment of a receptacle 222 according to the present invention for receiving plug 218 described above. Receptacle 222 differs from receptacle 22A of FIGS. 4A–D in that it does not include a plurality of electrically conductive detent contacts 146, 148, 150, 152, but instead includes conductive loops 249, 251 as described below. Receptacle 222 includes halves 202, 204 which are substantially the same as halves 102, 104 of receptacle 22A (except for bores 142, 144, 146, 148) and therefore not described in detail with reference to FIGS. 8A–8D. Halves 202, 204 form a central cavity 322 that extends substantially the entire length of receptacle 222 as best shown in FIG. 8C. Again, since cavity 322 is substantially the same as cavity 122 of receptacle 22A, the various surfaces and portions of cavity 322 are not repeated in the description of receptacle 222. Receptacle 222 further includes a bore 340 that extends through half 204 from an outer surface of receptacle 222 to central cavity 322. A spring loaded detent 352 is mounted within bore 340 such that a ball 341 of detent 352 (FIGS. 8C and 8D) is biased partially into cavity 322.

A conductor 295 extends from end $P_{H1}$ through an opening in receptacle 222 to form a loop 251 about central cavity 322. The other end of conductor 295 extends through another opening in receptacle 222 to end $P_{L1}$. Similarly, at another location within receptacle 222, a second conductor 297 extends from end $S_{H1}$ through an opening in receptacle 222 to form a loop 249 about central cavity 322. The other end of conductor 297 extends through another opening in receptacle 222 to end $S_{L1}$. Loops 249, 251 are embedded within the material of receptacle 222 just below the surface of cavity 322. In other words, loops 249, 251 are embedded into the inner, cylindrical wall of cavity 322 such that loops 249, 251 do not contact plug 218 when plug 218 is inserted into receptacle 222.

Figure 9:
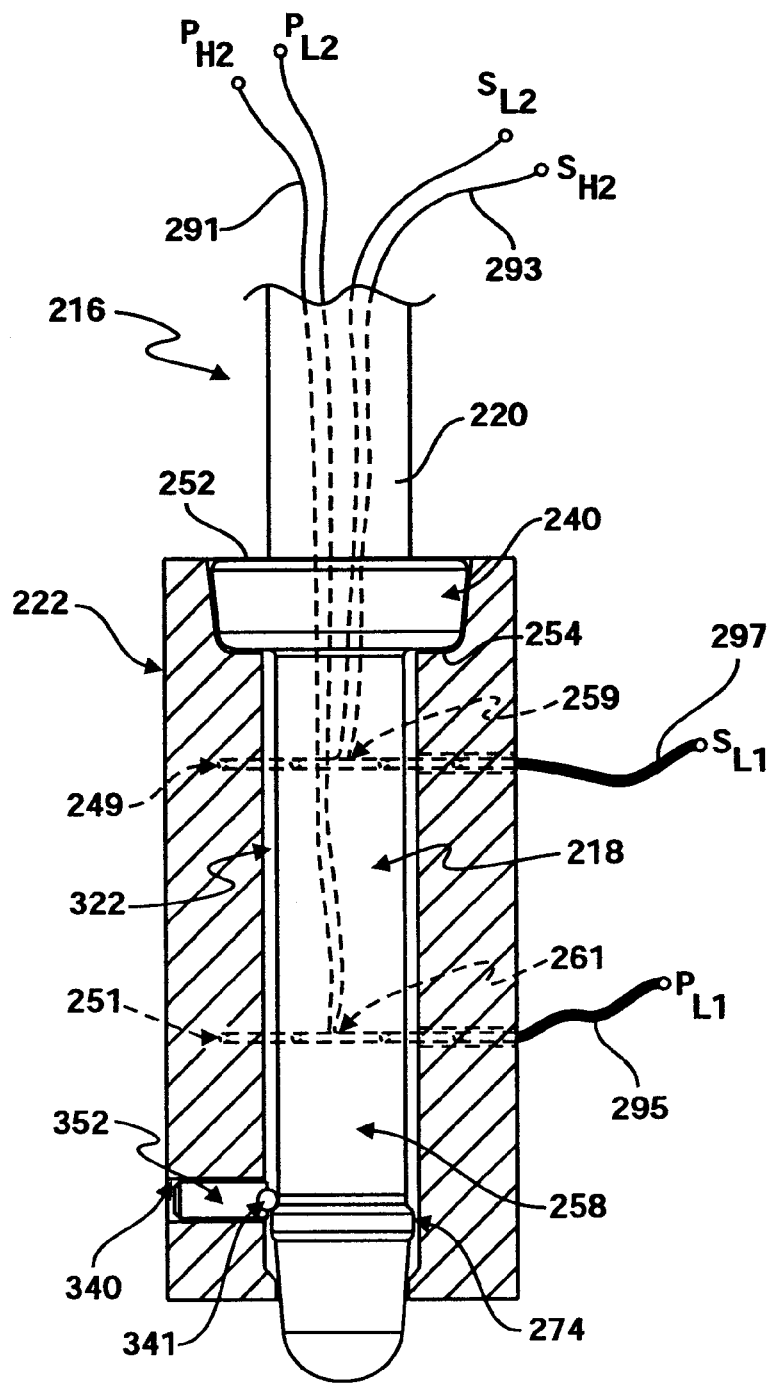
FIG. 9 is a partially fragmented, side elevational view, partly in section, of a portion of another embodiment of an equipment support apparatus according to the present invention.

Referring now to FIG. 9, plug 218 is shown in a seated position within receptacle 222. As shown, loop 259 of plug 218 lies substantially within the same plane as loop 249 of receptacle 222 such that the signal provided on conductor 297 is inductively coupled from loop 249 to loop 259 and conductor 293 having ends $S_{L2}$ and $S_{H2}$. Similarly, loop 261 lies substantially within the plane as loop 251 such that the signal provided on conductor 295 is inductively coupled from loop 251 to loop 261 and conductor 291 having ends $P_{H2}$ and $P_{L2}$. In this manner, power and control signals are provided from receptacle 222 to equipment support 216 even if dirt or other foreign material is built up in cavity 322 or on plug 218. Additionally, electricity is provided from receptacle 222 to equipment support 216 without requiring exposed, electrically conductive contacts.

As shown in FIG. 9, when plug 218 is in the seated position, ball 341 of detent 352 is urged outwardly toward extension 258 of plug 218 above retention ring 274. The outward biasing force of the spring (not shown) on ball 341 resists upward movement of plug 218 through interference with retention ring 274. Accordingly, the possibility of accidental removal of equipment support 216 from receptacle 222 is reduced.

Figure 10A:
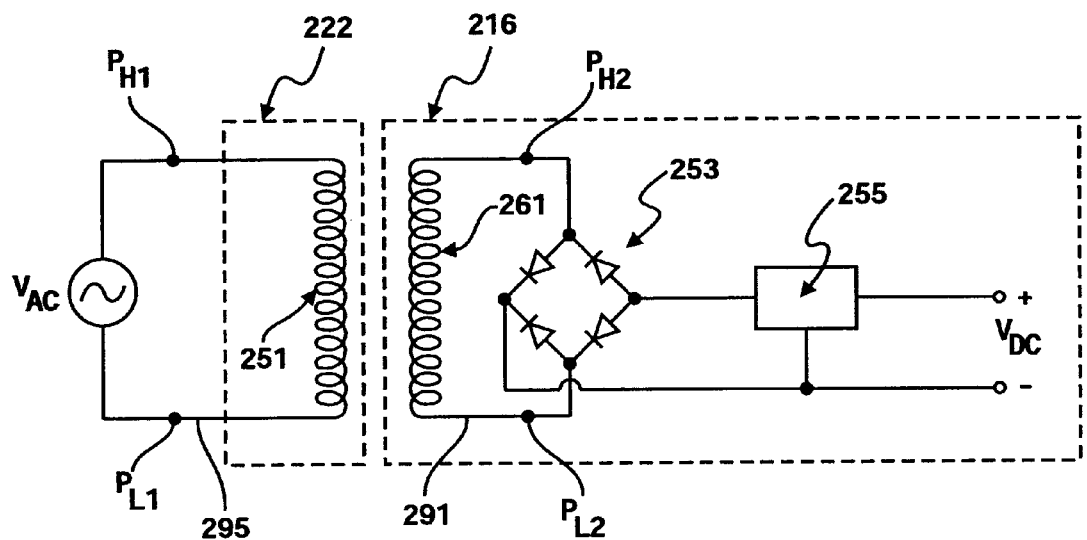
FIG. 10A is an electrical schematic diagram of a portion of the circuit of the equipment support apparatus shown in FIGS. 7–9.

FIG. 10A shows a basic schematic diagram of one possible circuit for supplying power from receptacle 222 to equipment support 216. An AC source ($V_{AC}$) is provided externally to the equipment support apparatus of the present invention. One side of supply $V_{AC}$ is connected to end $P_{H1}$ of conductor 295, and the other side is connected to end $P_{L1}$. Loop 251 is formed between ends $P_{H1}$ and $P_{L1}$ to form one side of the transformer shown in FIG. 10A. As shown, loop 251 is formed within receptacle 222 as described above.

Loop 261 (the other side of the transformer) is formed within equipment support 216 as described above. Conductor 291 from loop 261 extends to ends $P_{H2}$, $P_{L2}$ which are connected to a full-wave rectifier circuit 253 and a voltage regulator 255 to provide a DC output in a manner that is well-known to those skilled in the art. It should be understood that the signals provided on conductor 297 extending between ends $S_{H1}$ and $S_{L1}$ may be implemented using the same circuit as that described above.

Figure 10B:
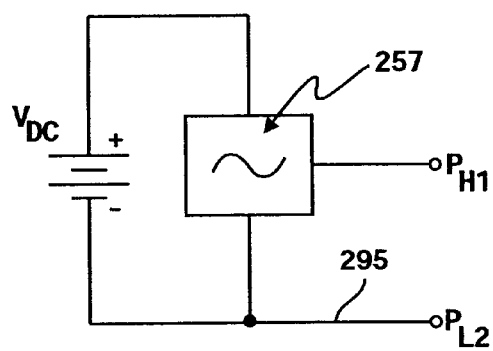
FIG. 10B is an electrical schematic diagram of an alternate power input circuit to replace a portion of the circuit of FIG. 10A.

FIG. 10B shows an alternate embodiment of the circuit of FIG. 10A. Specifically, instead of an AC power supply ($V_{AC}$), the circuit of FIG. 10B includes a DC power supply ($V_{DC}$) or a battery that is connected in a conventional manner to an oscillator circuit 257. The output of oscillator circuit 257 to nodes $P_{H1}$ and $P_{L1}$ is an AC signal similar to that provided from the AC power supply ($V_{AC}$). This signal may be passed through a transformer as described with reference to FIG. 10A, rectified by full wave rectifier 253, and regulated to form a DC signal at the output of regulator 255.

Figure 11A:
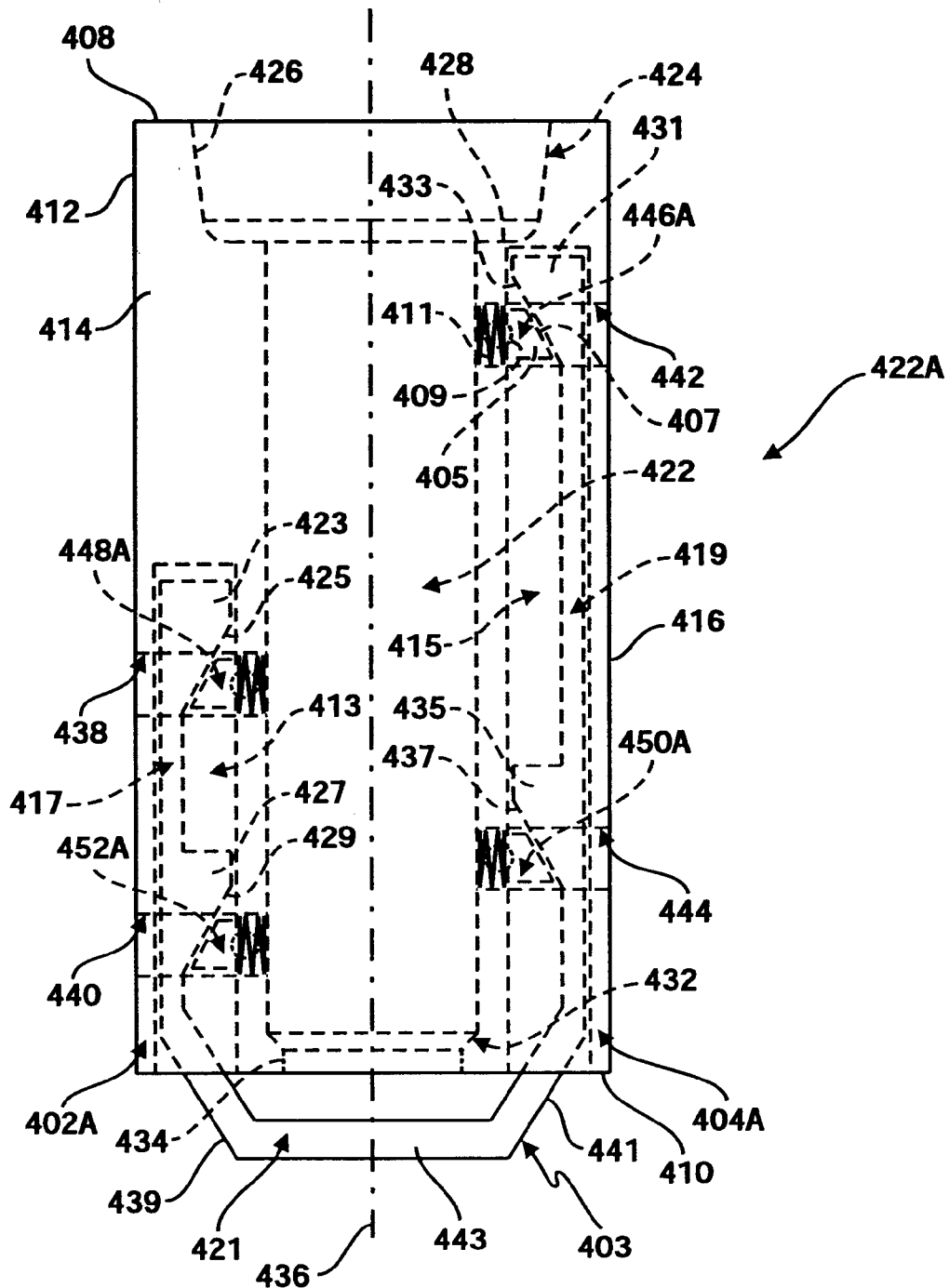
FIGS. 11A–C are side elevational views of alternate embodiments of a receptacle of an equipment support apparatus according to the present invention.
Figure 11B:
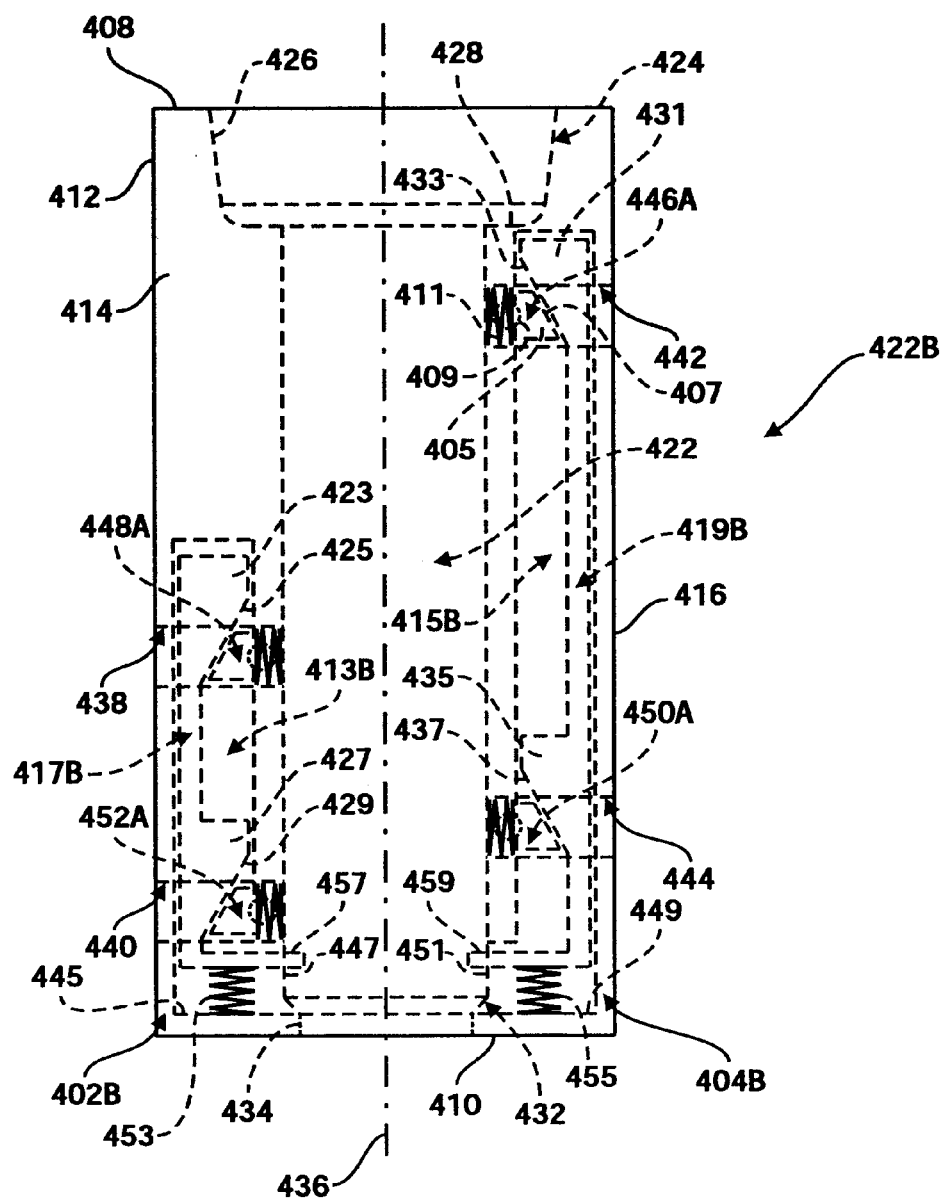
Figure 11C:
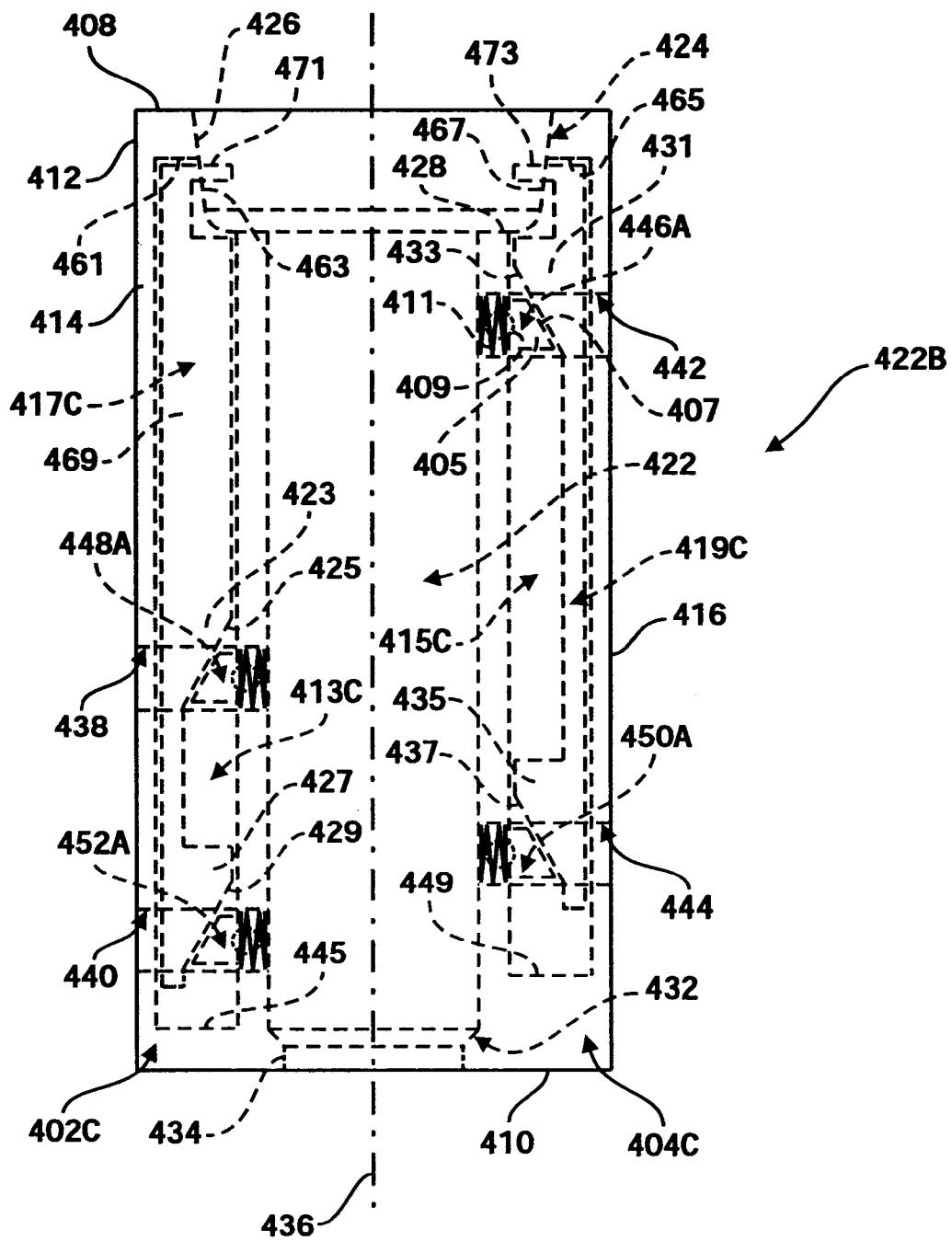

Referring now to FIGS. 11A–C, alternate embodiments of a receptacle of an equipment support apparatus according to the present invention are shown. Unlike receptacle 22A shown in FIGS. 4A–C, the receptacles of these embodiments do not include detent contacts that normally extend into the central cavity of the receptacle. Instead, as further described below, the detent contacts of these embodiments are actuated or moved to contacting positions within the cavity as a result of movement of plug 18A to the seated position within the cavity. Otherwise, several of the items shown in FIGS. 11A–C are similar to items depicted in FIGS. 4A–C, and are referred to using reference designations that have been increased by 300.

As shown in FIG. 11A, receptacle 422A generally includes first half 402A, second half 404A, and actuator 403. Like first half 102 of receptacle 22, first half 402A includes a pair of bores 438, 440 that contain detent contacts 448A, 452A, respectively. Similarly, second half 404A includes bores 442, 444 that contain detent contacts 446A, 450A, respectively. Each detent contact 446A, 448A, 450A, 452A is identical. For simplicity, only detent contact 446A is labeled with reference designations. Each detent contact 446A, 448A, 450A, 452A includes a body 405 having a cam surface 407 and a ball 409. Each body 405 is biased out of cavity 422, away from central axis 436 by a spring 411. First half 402A further includes a channel 413 that extends upwardly within first half 402A from an opening formed in bottom surface 410. Second half 404A includes a similar channel 415.

As shown, actuator 403 generally includes a first portion 417 situated within channel 413 of first half 402A, a second portion 419 situated within channel 415 of second half 404A, and an engagement portion 421 extending between first portion 417 and second portion 419. First portion 417 includes a first cam 423 having a first cam surface 425 and a second cam 427 having a second cam surface 429. Second portion 419 similarly includes a third cam 431 having a third cam surface 433 and a fourth cam 435 having a fourth cam surface 437. Engagement portion 421 includes a pair of angled segments 439, 441 and an engagement segment 443.

When plug 18A is inserted into cavity 412, balls 409 of detent contacts 446A, 448A, 450A, and 452A do not contact plug 18A because the balls are recessed into their respective bores 442, 438, 444, and 440. As plug 18A approaches the seated position, however, tip 48 engages engagement segment 443 of actuator engagement portion 421. As plug 18A is inserted farther downwardly, tip 48 moves actuator 403 downwardly such that first portion 417 and second portion 419 are moved downwardly in channels 413, 415, respectively. As first portion 417 and second portion 419 move downwardly, cam surfaces 425, 429, 433, and 437 of cams 423, 427, 431, and 435 respectively engage cam surfaces 407 of detent contacts 448A, 452A, 446A, 450A. As a result, detent contacts 446A, 448A, 450A, 452A are urged inwardly toward plug 18A against the biasing force of springs 411. Accordingly, when plug 18A is in the seated position, balls 409 of detent contacts 446A, 448A, 450A, 452A are in electrical connection with rings 94 of plug contacts 68, 70, 72, and 74, respectively. As should be apparent from the foregoing, actuator 403 may include a return mechanism such as a spring (not shown) to return actuator 403 to the position shown in FIG. 11A when plug 18A is removed from receptacle 422A. Alternatively, springs 411 of detent contacts 446A, 448A, 450A, and 452A may provide a sufficiently large biasing force to cause cam surfaces 407 of detent contacts 446A, 448A, 450A, and 452A to move along cam surfaces 433, 425, 437, 429 of cams 431, 423, 435, and 427, respectively, thereby urging actuator 403 upwardly into the position shown in FIG. 11A.

Referring now to FIG. 11B, another embodiment of a receptacle is shown. Receptacle 422B is generally similar to receptacle 422A, but includes a two-piece actuator that does not extend out of the assembly. More specifically, first half 402B includes a modified channel 413B that terminates at a lower end 445 rather than extending through bottom surface 410. Additionally, channel 413B includes an opening 447 that extends between channel 413B and cavity 422. Second half 404B similarly includes a modified channel 415B that terminates at a lower end 449 and includes an opening 451.

Receptacle 422B further includes a first actuator 417B, a first spring 453, a second actuator 419B, and a second spring 455. First actuator 417B is situated within channel 413B, and includes cams 423, 427 as described above with reference to FIG. 11A. Below cam 427, first actuator 417B includes an engagement portion 457 that extends through opening 447 into cavity 422. Spring 453 is positioned between end 445 of channel 413B and engagement portion 457, and biases first actuator 417B upwardly into the position shown in FIG. 11B. Second actuator 419B is situated within channel 415B, and includes cams 431, 435 as described above. Second actuator 419B also includes an engagement portion 459 that extends from below cam 435, through opening 451, and into cavity 422. Spring 455 biases engagement portion 459 (and second actuator 419B) upwardly into the position shown in FIG. 11B.

When plug 18A is inserted into cavity 422 of receptacle 422B, no electrical connections are made between plug 18A and receptacle 422B until plug 18A approaches the seated position. More specifically, as plug 18A reaches the lower portion of cavity 422, a pair of grooves (not shown) formed in plug 18A receive engagement portions 457, 459. When engagement portions 457, 459 reach a stop surface (not shown) formed in the grooves, further downward movement of plug 18A into cavity 422 moves first actuator 417B and second actuator 419B downwardly against the biasing force of springs 453, 455, respectively. This downward movement of first actuator 417B and second actuator 419B causes cams 423, 427, 431, and 435 to respectively move detent contacts 448A, 452A, 446A, and 450A into electrical connection with plug 18A as described above. When plug 18A is withdrawn from cavity 422, springs 411 and 453, 455 urge detent contacts 448A, 452A, 446A, and 450A, first actuator 417B, a and second actuator 419B back into the upward position shown in FIG. 11B. It should be understood that springs 453, 455 may be optional, since the biasing force of springs 411 may, without any other return mechanism, cam first actuator 417B and second actuator 419B into the upward positions.

FIG. 11C shows yet another receptacle 422C according to the present invention. Receptacle 422C is similar to receptacle 422B in that it includes a two-piece actuator that does not extend out of the assembly. Unlike receptacle 422B, receptacle 422C includes a two-piece actuator that is engaged by stop 40 of plug 18A. More specifically, first half 402C includes a modified channel 413C that terminates at a lower end 445 and at an upper end 461. An opening 463 is formed adjacent upper end 461 between channel 413C and enlarged diameter portion 424 of cavity 422. Second half 404C similarly includes a modified channel 415C that terminates at an upper end 465 and includes an opening 467.

First actuator 417C of receptacle 422C is situated within channel 413C, and includes cams 423, 427 as described above with reference to FIG. 11A. First actuator 417C further includes an elongated body portion 469 that extends from cam 423 and terminates at an engagement portion 471 that extends through opening 463 into enlarged diameter portion 424 of cavity 422. Second actuator 419C is similarly situated within channel 415C, and includes cams 431, 435 as described above. Second actuator 419C also includes an engagement portion 473 that extends from above cam 431, through opening 467, and into enlarged diameter portion 424.

When plug 18A is inserted into cavity 422 of receptacle 422C, no electrical connections are made between plug 18A and receptacle 422C until plug 18A approaches the seated position. More specifically, as plug 18A reaches the lower portion of cavity 422, a pair of openings or grooves (not shown) formed in stop 40 of plug 18A receive engagement portions 471, 473. When engagement portions 471, 473 reach a stop surface (not shown) formed in the grooves, further downward movement of plug 18A into cavity 422 moves first actuator 417C and second actuator 419C downwardly. This downward movement of first actuator 417C and second actuator 419C causes cams 423, 427, 431, and 435 to respectively move detent contacts 448A, 452A, 446A, and 450A into electrical connection with plug 18A as described above. When plug 18A is withdrawn from cavity 422, springs 411 urge detent contacts 448A, 452A, 446A, and 450A, first actuator 417C, and second actuator 419C back into the upward position shown in FIG. 11C.

The foregoing description of the invention is illustrative only, and is not intended to limit the scope of the invention to the precise forms set forth. Although the invention has been described in detail with reference to certain illustrative embodiments, variations and modifications exist within the scope and spirit of the invention as described and defined in the following claims. For example, one skilled in the art could readily adapt interfaces, pendants, and other equipment with conventional connectors so that the various pieces of equipment are modular and easily replaceable. Moreover, the entire support body of an equipment support device according to the present invention could be formed from flexible, gooseneck material to provide additional flexibility. It should be further understood, that the basic concept of the present invention may be adapted to other uses such as with headwall units, power columns, overbed tables, and wheelchairs.

What is claimed is:

1. An equipment support for use with a patient assist apparatus having a signal source providing a first and a second signal, the support including:

a receptacle adapted to mount to the patient assist apparatus, the receptacle including a first contact adapted to receive the first signal, a second contact adapted to receive the second signal, and a cavity; and a support body having an equipment end and a plug for being removably inserted into the cavity, the plug having a body including a first contact connected to a first conductor and a second contact connected to a second conductor, the first and second conductors extending to the equipment end of the support body and being adapted for connection to a first piece of equipment mounted to the equipment end of the support body;

wherein the first plug contact contacts the first receptacle contact and the second plug contact contacts the second receptacle contact only when substantially the entire plug body is inserted into the cavity.

2. The support of claim 1, wherein the receptacle cavity is substantially cylindrical.

3. The support of claim 1, wherein the receptacle contacts are detents.

4. The support of claim 1, wherein the support body is substantially cylindrical.

5. The support of claim 4, wherein each of the plug contacts includes a ring portion having a diameter that is greater than a diameter of the body, the ring portions cooperating with the receptacle contacts to resist removal of the plug from the receptacle when substantially the entire plug body is inserted into the cavity.

6. The support of claim 1, wherein the support body further includes a first section that is telescopically connected to a second section.

7. The support of claim 1, further including a flexible portion extending from the equipment end of the support body.

8. The support of claim 7, wherein the first and second conductors are adapted for connection to a second piece of equipment mounted to a free end of the flexible portion.

9. The support of claim 1, wherein the plug body is substantially cylindrical.

10. The support of claim 9, wherein the plug further includes an annular stop having a diameter that is greater than a diameter of the plug body, the stop being seated within an enlarged diameter portion of the cavity when substantially the entire plug body is inserted into the cavity.

11. The support of claim 1, wherein the plug contacts are annular.

12. The support of claim 1, wherein the cavity has a central axis, the first receptacle contact extending into the cavity at a first location along the central axis, and the second receptacle contact extending into the cavity at a second location along the central axis.

13. The support of claim 12, wherein the receptacle further includes a third contact extending into the cavity at a third location along the central axis, and a fourth contact extending into the cavity at a fourth location along the central axis, the plug body further including third and fourth contacts that contact the third and fourth receptacle contacts, respectively, only when substantially the entire plug body is inserted into the cavity.

14. The support of claim 13, wherein the plug body is cylindrical and the plug contacts are annular, the plug further including annular insulators separating the plug contacts.

15. The support of claim 13, wherein the second location is a first distance from the first location, the third location is a second distance from the second location, and the fourth location is a third distance from the third location, each of the first, second and third distances being different from the other distances.

16. The apparatus of claim 1, wherein the plug is included in a plug end of the support body.

17. The apparatus of claim 1, wherein the plug is integral with an end of the second body.

18. The apparatus of claim 1, wherein the plug fails to extend beyond the end of the support body.

19. The apparatus of claim 1, wherein the cavity is sized and shaped to receive an end of the support body therein.

20. The apparatus of claim 1, wherein distance between the first plug contact and the equipment end is always less than the distance between second plug contact and the equipment end.

21. The apparatus of claim 1, wherein the support body is at least partially received in the cavity.

22. A hospital bed, including
   a frame for supporting a patient, the frame including a receptacle having a first contact connected to a first signal, a second contact connected to a second signal, and a cavity; and
   an equipment support having a body with a first equipment mount adjacent one end, a plug connected to the other end for removable insertion into the receptacle cavity, and a pair of conductors extending from the first equipment mount to the plug, the plug including a first contact connected to one of the conductors and a second contact connected to the other conductor;
   wherein the first and second plug contacts respectively engage the first and second receptacle contacts, thereby providing the first and second signals through the conductors to the equipment mount, as the plug is inserted into the cavity.

23. The bed of claim 22, wherein the frame includes a plurality of receptacles to permit placement of the equipment support at a plurality of different locations about the bed.

24. The bed of claim 22, wherein each of the receptacle contacts includes an electrically conductive ball and a spring that biases the ball into the cavity.

25. The bed of claim 24, wherein each of the balls is disposed within a respective bore formed in the receptacle.

26. The bed of claim 24, wherein each of the plug contacts includes a ring portion having a diameter that is greater than a diameter of the plug, the ring portions cooperating with the balls to resist removal of the plug from the receptacle when the plug is fully inserted into the cavity.

27. The bed of claim 22, wherein the support body is a pole.

28. The bed of claim 22, wherein the support body further includes a first section that is telescopically connected to a second section.

29. The bed of claim 22, further including a flexible portion extending from the one end of the support body.

30. The bed of claim 29, wherein the first and second conductors extend to a second equipment mount connected to a free end of the flexible portion.

31. The bed of claim 30, further including an interface connected to the first equipment mount and a pendant connected to the second equipment mount.

32. The bed of claim 22, wherein the plug further includes a stop that engages the receptacle to prevent further insertion of the plug into the cavity when the plug is fully inserted into the cavity.

33. The bed of claim 22, wherein the plug includes a body having an outer surface, the plug contacts being annular and protruding from the outer surface.

34. The bed of claim 22, wherein the receptacle further includes a third contact and a fourth contact, and the plug further includes a third contact and a fourth contact that contact the third and fourth receptacle contacts, respectively, as the plug is inserted into the cavity.

35. The bed of claim 34, wherein the plug contacts are separated by insulators.

36. The bed of claim 34, wherein the plug contacts are unequally spaced apart from one another along a length of the plug to prevent simultaneous contact between the plug contacts and their respective receptacle contacts when the plug is being inserted and removed from the cavity.

37. The apparatus of claim 22, wherein the plug is included in a plug end of the equipment support.

38. The apparatus of claim 22, wherein the plug is integral with an end of the equipment support.

39. The apparatus of claim 22, wherein the plug fails to extend beyond the end of the equipment support.

40. The apparatus of claim 22, wherein the cavity is sized and shaped to receive an end of the equipment support therein.

41. The apparatus of claim 22, wherein distance between the first contact and the equipment mount is always less than the distance between second contact and the equipment mount.

42. The apparatus of claim 22, wherein the equipment support is at least partially received in the cavity.

43. A patient assist apparatus, including:
   a frame;
   a receptacle mounted to the frame, the receptacle having electrical contacts that receive a signal;
   a pole having a piece of equipment connected to one end and a plug connected to the other end, the plug having electrical contacts connected to the equipment that are in electrical communication with the receptacle contacts when the plug is inserted into the receptacle, thereby providing the signal to the equipment.

44. The apparatus of claim 43, wherein the frame includes a plurality of receptacles to permit placement of the pole at a plurality of different locations.

45. The apparatus of claim 43, wherein the plug is included in a plug end of the pole.

46. The apparatus of claim 43, wherein the plug is integral with an end of the pole.

47. The apparatus of claim 43, wherein the plug fails to extend beyond the end of the pole.

48. The apparatus of claim 43, wherein the cavity is sized and shaped to receive an end of the pole therein.

49. The apparatus of claim 43, wherein the pole is at least partially received in the cavity.

* * * * *

UNITED STATES PATENT AND TRADEMARK OFFICE
CERTIFICATE OF CORRECTION

PATENT NO.     : 6,704,956 B2
DATED          : March 16, 2004
INVENTOR(S)    : Riley et al.

It is certified that error appears in the above-identified patent and that said Letters Patent is hereby corrected as shown below:

<u>Title page,</u>
Item [75], Inventors, second inventor should read -- Troy D. Acton --.

Signed and Sealed this

Eleventh Day of April, 2006

JON W. DUDAS
*Director of the United States Patent and Trademark Office*